United States Patent [19]
Kennedy et al.

[11] Patent Number: 5,614,198
[45] Date of Patent: Mar. 25, 1997

[54] BOWMAN-BIRK INHIBITOR COMPOSITIONS FOR TREATMENT OF INFLAMMATORY DISEASE

[75] Inventors: Ann R. Kennedy, Wynnewood; Paul C. Billings, Swarthmore, both of Pa.

[73] Assignee: The Trustees of the University of Pennsylvania, Philadelphia, Pa.

[21] Appl. No.: 507,044

[22] Filed: Jul. 25, 1995

[51] Int. Cl.$^6$ .................................................. A61K 35/78
[52] U.S. Cl. ........................................................ 424/195.1
[58] Field of Search ........................... 424/195.1, 94.63; 514/2

[56] References Cited

U.S. PATENT DOCUMENTS 4,793,996  12/1988  Kennedy et al. .................... 424/195.1
5,217,717  6/1993   Kennedy et al. .................... 424/195.1

OTHER PUBLICATIONS

Baturay et al., "Pyrene acts as a cocarcinogen with the carcinogens benzo[a]pyrene, β-propiolactone and radiation in the induction of malignant transformation in cultured mouse fibroblasts; soybean extract containing the Bowman-–Birk Inhibitor acts as an anticarcinogen," *Cell Biology and Toxicology* 1986, 2, 21–32.

Birk et al., "Separation of a tribolium–protease inhibitor from soybeans on a calcium column," *Biochim. Biophys. Acta* 1963, 67, 326–328.

Bowman, "Differentiation of Soy Bean Antitryptic Factors," *Proc. Soc. Exptl. Med.* 1946, 63, 547–550.

Bradford, "A rapid and sensitive method for the quantitation of microgram quantities of protein utilizing the principle of protein–dye binding," *Anal. Biochem.* 1976, 72, 248–254.

Frenkel et al., "Chymotrypsin–specific protease inhibitors decrease $H_2O_2$ formation by activated human polymorphonuclear leukocytes," *Carcinogenesis* 1987, 8(9), 1207–1212.

Kennedy et al., *Anticarcinogenesis and Radiation Protection*, edited by Cerutti et al., Plenum Pub. Co. 1987, pp. 285–295.

Messadi et al., "Inhibition of Oral Carcinogenesis by a Protease Inhibitor," *JNCI* 1986, 76, 447–452.

Perlmann et al., "Proteolytic Enzymes," *Methods in Enzymology* 1970, 19, 860–861.

St. Clair et al., "Suppression of Dimethylhydrazine–induced Carcinogenesis in Mice by Dietary Addition of the Bowman–Birk Protease Inhibitor," *Cancer Res.* 1990, 50, 580–586.

Weed et al., "Protection against dimethylhydrazine–induced adenomatous tumors of the mouse colon by the dietary addition of an extract of soybeans containing the Bowman-–Birk protease inhibitor," *Carcinogenesis* 1985, 6, 1239–1241.

Yavelow et al., "Nanomolar concentrations of Bowman-–Birk soybean protease inhibitor suppress x–ray–induced transformation in vitro," *Proc. Natl. Acad. Sci. USA* 1985, 82, 5395–5399.

Yavelow et al., "Bowman–Birk soybean protease inhibitor as an anticarcinogen," *Cancer Res.* 1983, 43, 2454–2459.

*Primary Examiner*—Raymond Henley, III
*Attorney, Agent, or Firm*—Law Offices of Jane Massey Licata

[57] ABSTRACT

A composition containing a Bowman-Birk Inhibitor for the treatment of inflammation is provided. Methods of using this composition in the treatment of IBD and hepatic inflammation are also provided.

4 Claims, 5 Drawing Sheets

BOWMAN-BIRK INHIBITOR COMPOSITIONS FOR TREATMENT OF INFLAMMATORY DISEASE

This invention was made in the course of research sponsored by the National Institutes of Health. The U.S. Government may have certain rights in this invention.

BACKGROUND OF THE INVENTION

This invention relates to a composition and method for the treatment of inflammatory disease.

Protease inhibitors are classes of compounds commonly found in many different types of foods, such as legumes, cereals, nuts, fruits and vegetables. One of the best characterized protease inhibitors is the Bowman Birk Inhibitor (BBI) which is derived from soybeans. It is a 71 amino acid chain with 7 disulfide bonds that binds 1:1 with trypsin and chymotrypsin at different binding sites and has a molecular weight of approximately 8000.

In vivo and in vitro studies of protease inhibitors, and BBI in particular, have shown them to be effective anticarcinogenic agents. It has been shown that the enzymeinhibitor described by Bowman, *Proc. Soc. Exptl. Med.* 1946, 63, 547 and Birk et al., *Bull. Res. Council Israel* 1962, Sec. 1, 11, 48 and *Biochim. Biophys.* Acta 1963, 67, 326, and subsequently referred to as the Bowman-Birk Inhibitor (BBI), possesses certain physiological activity that prevents, or at least greatly reduces, radiologically or chemically induced malignant transformation of cells in culture and in experimental animals.

Yavelow et al., *Proc. Natl. Acad. Sci. USA* 1985, 82, 5395–5399, reported that a crude soybean extract, if defatted with acetone, effectively blocked cell transformation in vitro. These observations, with epidemiological data, suggested BBI as a putative dietary anticarcinogen, particularly with respect to colon cancer.

Weed et al., *Carcinogenesis* 1985, 6, 1239–1241, disclose that an extract of soybeans containing the Bowman-Birk protease inhibitor added to the diet of dimethylhydrazine (DMH)-treated mice resulted in a significant suppression of adenomatous tumors of the colonic mucosa. DMH-induced colon cancer in mice is generally regarded as an excellent animal model for the human disease, with carcinogen treatment inducing adenocarcinomas of the colon and rectum which are similar to the tumors arising in the human colon suggesting the possibility that a dietary additive of the sort studied might confer some protection against the development of human colon cancer without undesirable side effects. The BBI extract and methods for its preparation were as described by Yavelow et al., *Cancer Res.* 1983, 43, 2454–2459; *Proc. Natl. Acad. Sci. USA* 1985, 82, 5395–5399.

Messadi et al., *JNCI* 1986, 76, 447–452 demonstrated that a soybean extract containing the protease inhibitor BBI suppresses 7, 12-dimethyl-benz[a]anthracene (DMBA)-induced carcinogenesis in the hamster cheek pouch. This oral cancer model has the same histopathology, growth pattern and precancerous lesions as the most common form of human oral cancer, squamous cell carcinoma. It was shown in this study that hamster cheek pouch carcinogenesis can be inhibited by BBI and suggested that human oral carcinogenesis might respond to BBI in a comparable manner. The BBI preparation used in this study was a crude extract of the inhibitor prepared as described by Yavelow et al., *Proc. Natl. Acad. Sci. USA* 1985, 82, 5395–5399.

Baturay et al., *Cell Biology and Toxicology* 1986, 2, 21–32 disclose that a BBI preparation, wherein a crude soybean extract is defatted with acetone, suppresses radiation and chemically induced transformation in vitro, with or without enhancement by the co-carcinogen, pyrene. Yavelow et al., 1985, show that either pure BBI or the BBI extract prepared in accordance with their methods suppresses radiation induced transformation in C3H10T1/2 cells. Kennedy et al., 1984, report that either pure BBI or the BBI extract prepared in accordance with their method reduce the levels of chromosome abnormalities in cells of patients with Bloom's syndrome (a genetic disease in which the high levels of chromosome abnormalities are thought to predispose the patients to a higher than normal cancer incidence). Still, other studies suggest that soybean-derived protease inhibitors can have suppressive effects on skin, breast and liver carcinogenesis in vivo.

Kennedy et al. in *Anticarcinogenesis and Radiation Protection*, edited by Cerutti et al., Plenum Pub. Co. 1987, pp. 285–295, disclose that BBI suppresses carcinogenesis in various systems using a crude BBI extract prepared by defatting soybeans with acetone. Their results suggested that very low concentrations of BBI-type protease inhibitor preparations would be effective as chemopreventive agents for colon cancer. There was no evidence to suggest that the use of protease inhibitors as chemopreventive agents would be complicated by possible toxicity problems.

St. Clair et al., *Cancer Res.* 1990, 50, 580–586, report that the addition of 0.5% or 0.1% semi-purified BBI to the diet of DMH-treated mice resulted in a statistically significant suppression of angiosarcomas and nodular hyperplasia of the liver and colon carcinogenesis. The results of this study also indicate that BBI, included as 0.5% of the diet or less had no adverse effect upon the health of the mice but had the capacity to suppress liver and colon carcinogenesis.

A soybean extract enriched in BBI, termed Bowman-Birk inhibitor concentrate (BBIC), has achieved Investigational New Drug Status from the Food and Drug Administration and human trials to evaluate it as a human cancer chemotherapeutic agent have begun.

Frenkel et al. *Carcinogenesis* 1987, 8(9), 1207–1212 monitored formation of $H_2O_2$ by 12-O-tetradenoyl-phorbol-13-acetate (TPA)-activated polymorphonuclear leukocytes (PMNs) in the absence or presence of protease inhibitors and/or superoxide dismutase (SOD). Protease inhibitors tested include potato inhibitors 1 (PtI-1) and 2 (PtI-2), a chymotrypsin inhibitory fragment of PtI-2 (PCI-2), chicken ovoinhibitor (COI), turkey ovomucoid ovoinhibitor (TOOI), Bowman-Birk inhibitor (BBI), lima bean inhibitor (LBI) and soybean (Kunitz) trypsin inhibitor (SPTI). The order of activity, as measured by inhibition of $H_2O_2$ formation, was PtI-1≧PCI-2>PtI-2>COI>BBI>TOOI>LBI>SBTI thus showing that protease inhibitors specific for chymotrypsin, but not those that are trypsin-specific, are capable of inhibiting formation of active oxygen species during the oxidative burst of stimulated human PMNs. BBI was characterized as an inhibitor of both chymotrypsin and trypsin.

Perlmann et al., *Methods in Enzymology* 1970, 19, 860–861, have described an elaborate method for obtaining BBI from a defatted soybean extract.

U.S. Pat. No. 4,793,996 (Kennedy et al.) discloses a process comprising treating soybeans with acetone, followed by ethanol extraction and acetone precipitation for obtaining BBI. The soybeans may be defatted prior to acetone treatment. In addition, BBI may be further purified by conventional techniques. Kennedy et al. discovered that in the conventional process for preparing BBI from soybeans, a factor remained which adversely affected the ability of BBI to inhibit the malignant transformation of cells. If the factor was removed, the resulting BBI product was capable of inhibiting the malignant transformation of cells. It was found to be possible to remove this factor by treating the soybeans with acetone prior to the ethanol extraction step taught by Perlmann et al.

Kennedy et al. teach that it is unnecessary to carry out a procedure requiring complete purification of the extract to the point where the product contains only a single protein. Instead, they found it effective to stop the purification procedure at a point where a crude inhibitor extract is obtained. This crude extract is itself edible and can be used as an inhibitor of malignant transformation of cells, for example, by oral ingestion. Kennedy et al. disclose a process for preparing a crude soybean extract containing an inhibitor of malignant cell transformation which comprises defatting soybeans and extracting said inhibitor from said defatted soybeans.

While the anti-carcinogenic activity of BBI is known, its anti-inflammatory effects were, until now, unknown.

SUMMARY OF THE INVENTION

An object of the present invention is to provide a BBI composition for the treatment of inflammation.

Another object of the present invention is to provide a method for treating inflammatory bowel disease in an animal comprising administering an effective amount of BBI to an animal having an inflammatory bowel disease.

Another object of the present invention is to provide a method of treating hepatic inflammation in an animal comprising administering an effective amount of BBI to an animal having hepatic inflammation.

When lanes 4 and 6 are compared to lane 1, it can be observed that both BBI and BBIC effectively inhibit the proteolytic activity of trypsin. These results indicate that BBI inhibits the proteolytic activity in the UC sample by 2.8 fold, while BBIC inhibits the activity by 3.1 fold. The results were quantitated by scanning densitometry.

Figure 4:
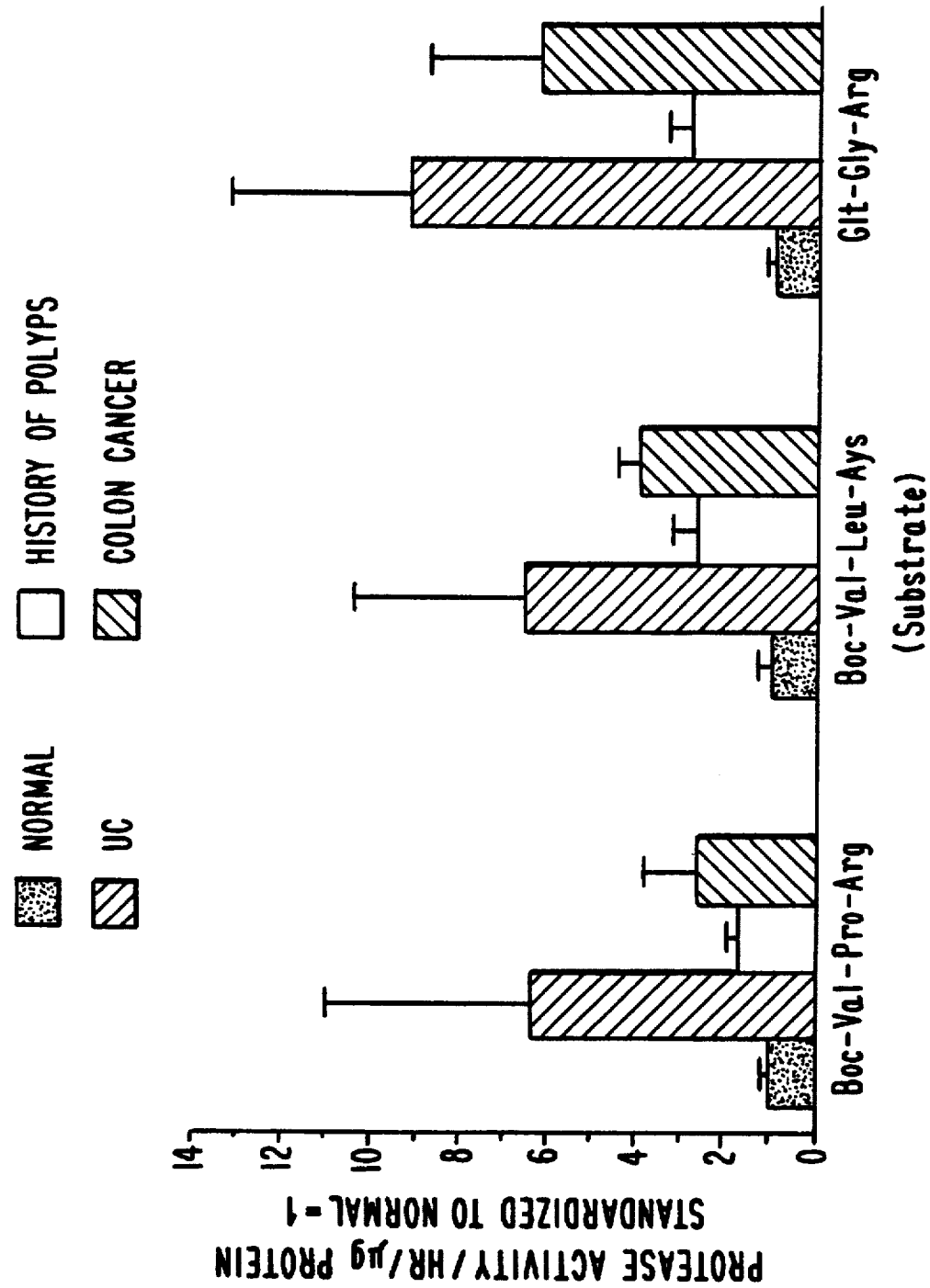

FIG. 4 shows levels of proteolytic activity in colon mucosal biopsy sections taken from normal individuals and those at elevated risk of colon cancer development. The tissue samples from those at elevated risk of colon cancer development represent normal appearing regions of colonic mucosa in patients with: 1) ulcerative colitis; 2) a history of having one or more adenomatous polyps endoscopically resected, i.e. a history of polyps; and 3) a history of having had colon cancer. These data indicate that there are elevated levels of certain types of proteolytic activities in colonic mucosal tissue taken from individuals at higher than normal risk for developing colon cancer.

Figure 5:
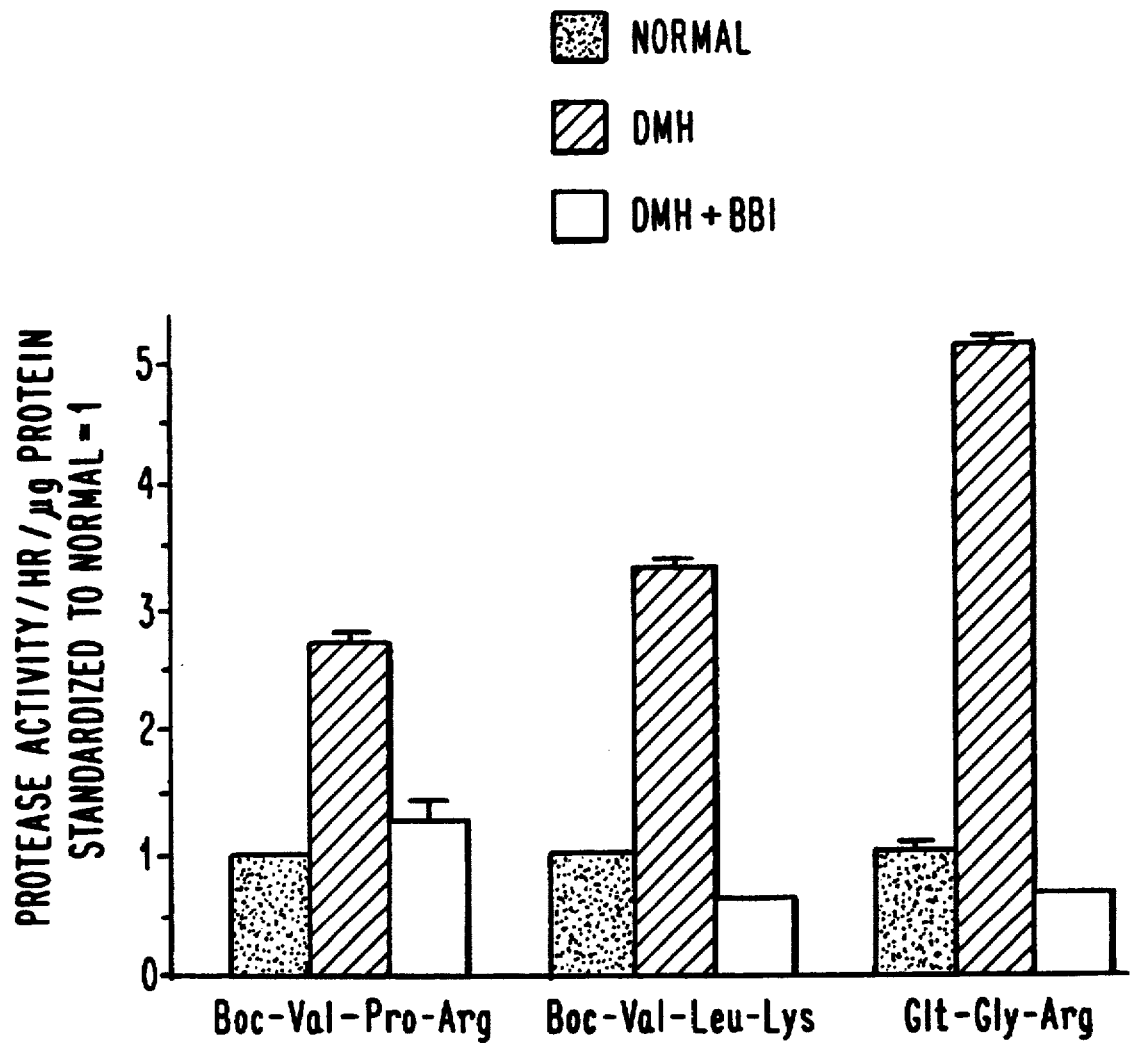

FIG. 5 provides data showing reduction of proteolytic activities, as measured by three different substrates in rats treated with DMH+BBI compared to those receiving DMH alone. Colon mucosal biopsy sections were taken from animals one month after the last dose of DMH was administered to animals in colon carcinogenesis studies. In normal appearing areas of colon mucosa, DMH treatment results in a significant elevation in levels of proteolytic activities compared to the levels observed in normal animals, while BBI treatment of these DMH exposed normal appearing areas results in levels of activity which are not significantly different from control animals who were not exposed to DMH.

DETAILED DESCRIPTION OF THE INVENTION

Inflammatory bowel diseases (IBD) were described early in the 19th century and were later broken down into the two major categories, ulcerative colitis and Crohn's disease. There is a small subset of IBD cases which do not fall into either category as well as some other rare conditions that are classified as types of IBD as well. There is considerable variation in the estimates of IBD in the United States, but most studies predict that there are between one and two million affected, with 20,000 to 25,000 new cases per year. In caucasians, there is a bimodal distribution of age of onset with a peak at 15–30 years of age for Crohn's disease and 20–35 years of age for ulcerative coliris. The second peak for this disease occurs at about age 70. Disease which starts at a younger age is usually more severe. Industrialized countries, especially the U.S. and northern Europe have the highest rates of IBD, while Japan and South American countries have the lowest incidence.

Ulcerative colitis is a disease that primarily affects the mucosal lining of the colon but can affect the distal portion of the ileum. The disease can go into remission but will usually recur. The clinical signs typically involve abdominal cramping, fatigue, weight loss, bloody diarrhea and/or constipation. In fulminating cases, ulcerative colitis can be life-threatening. Only about 10% of the patients will have lesions outside of the intestine and about 20–25% of the patients will have a colectomy after 10 years with the disease. There can also be associated disease of the skin, liver, biliary tract, joints, blood dyscrasias and ocular lesions. Endoscopic and histopathologic evaluation of ulcerative colitis patients show a symmetrical, continuous inflammation of the colon mucosa. The disease usually starts in the rectum and progresses towards the anus and the ileum. The condition is continuous. There is a cyclical pattern of erosion and inflammation followed by healing and there is often an inflammatory exudate on the mucosal surface. The acute phase of the disease is characterized by crypt abscesses and ulcerations extending to the muscularis layer with a prominent infiltration of inflammatory cells. The chronic phase has additional fibrosing and thickening of the gut wall with lymphoplasmacytic infiltration and distortion of the mucosal architecture. The etiology of ulcerative coliris is unknown.

Crohn's disease is a chronic recurring process that involves all of the layers of the bowel wall and can occur anywhere in the gastrointestinal tract from the mouth to the anus. Clinical signs typically involve diarrhea (with or without blood), abdominal pain and weight loss. There is often perianal involvement with fistula formation. There may also be severe renal disease associated with Crohn's disease. On endoscopy and histopathology, Crohn's disease is a patchy, segmental disease with distinct borders to the lesion. The intestine becomes thickened and fibrotic and in chronic cases will be stiff like a rubber hose, with long serpentine fissures in the gut lining. The chronic transmural inflammation, intramural sinuses, lymphoid aggregates, and non-caseating granulomas are principal characteristics of Crohn's disease. The etiology of Crohn's disease is unknown.

That IBD is associated with increased risk of colon cancer has been known since the early part of this century. Survey data indicate that ulcerative colitis is slightly more likely to lead to the development of colon cancer than Crohn's disease and that the chance of developing cancer increases with time from the initial bout of illness. There is not an increased risk of cancer at other sites outside of the colon unless there is Crohn's disease of the small bowel. In patients with Crohn's disease of the small intestine, the risk of adenocarcinoma of the small intestine is 50 to 100 times that of the general population. In retrospective studies, the magnitude for the risk of colon cancer as compared to the general population is 3 to 30 fold for ulcerative coliris and about 4 to 20 fold for Crohn's disease patients. The variation in estimates of risk are due to the type of population studies, the length and method of study and other epidemiological factors. The extent and duration of colonic inflammation appear to be the major risk factors for cancer in IBD patients, with the risk greatly increasing 8 to 10 years following the initial bout of disease. It is believed that the effects of chronic inflammation lead to the development of colon tumors. Diagnosing cancer in IBD patients is complicated by IBD masking the cancer symptoms. Typically, IBD patients are followed with yearly endoscopic examinations and biopsies to observe for the development of dysplasias and cancers.

Current areas of research on etiology include genetics, metabolic defects, mucosal defects, immunological disturbances, autoimmunity and dietary factors. Areas of current interest in therapeutic development include immunomodulation, utilization of agents with highly specific targets such as cytokines, T cells and antioxidants.

In the present invention, compositions comprising BBI for the treatment of inflammation are provided. In a preferred embodiment, these compositions further comprise a pharmaceutically acceptable carrier. These compositions are particularly useful in the treatment of inflammatory bowel disease and hepatic inflammation. By "BBI" it is meant to include any Bowman Birk Inhibitor or Bowman Birk Inhibitor product, including, but not limited to, BBI prepared by methods known in the art and BBI concentrates prepared in accordance with the method of U.S. Pat. No. 5,217,717. Also provided are methods of treating inflammation in an animal by administering an effective amount of a composition comprising BBI. By "animal" it is meant to include, but is not limited to, any mammal including humans.

Administration of an effective amount of the claimed compositions, either as a prophylactic dietary supplement or a pharmaceutical, is within the teachings of the invention. The term "effective amount" refers to an amount which prevents expression of certain types of proteolytic activities, for example, the 44 kDa protein. Such an amount can be determined by those of skill in the art in accordance with known methods. Compositions of the present invention may be administered parenterally, rectally, topically, transdermally or orally, preferably orally. Examples of pharmaceutical or prophylactic dietary supplement formulations include, but are not limited to, syrups, suspensions, emulsions, tablets, capsules, lozenges and mouthwashes.

One embodiment of the invention is a liquid formulation comprising a suspension or solution of the composition in a pharmaceutically acceptable liquid carrier. Suitable liquid carriers include, but are not limited to, ethanol, glycerin, non-aqueous solvents such as polyethylene glycols, oils or water with a suspending agent, preservatives, flavorings or coloring agents, or any suitable combination thereof.

Another liquid formulation of a BBI composition useful in the present invention is a stable mouthwash solution that provides extended mucosal contact time, is palatable, easy to administer and suitable for low cost mass production. A saliva substitute provides the solution with the necessary viscosity to increase mucosal contact time and bioavailability, and has been shown to provide sustained release of many compounds. In one formulation, BBI Concentrate (BBIC) product, a saliva substitute such as sorbitol, carboxymethylcellulose, or methylparaben and water are included.

In another embodiment, a composition in the form of a tablet is prepared using any suitable pharmaceutical carrier routinely used for preparing solid formulations. Examples of such carriers include, but are not limited to, magnesium stearate, starch, lactose, sucrose and cellulose.

Compositions in the form of capsules are prepared using routine encapsulating procedure. For example, pellets, granules or powder containing a composition of the instant invention can be prepared using standard carriers and then filled into a hard gelatin capsule. Alternatively, a dispersion or suspension can be prepared using any suitable pharmaceutical carrier(s) and the dispersion or suspension is then filled into a soft gelatin capsule. Suitable pharmaceutical carriers include, but are not limited to, aqueous gums, cellulose, silicates and oils.

In yet another embodiment, a composition for parenteral administration is formulated as a solution or suspension. This solution or suspension will generally include the composition of the instant invention in a sterile aqueous carrier or parenterally acceptable oil. Examples of parenterally acceptable oils include, but are not limited to, polyethylene glycol, polyvinyl pyrrolidone, lecithin, arachis oils and sesame oil. Alternatively, the solution can be lyophilized and then reconstituted with a suitable solvent just prior to administration.

A hapten-induced model for chronic colitis has been developed based on the theory that there is an immunological component in the etiology of IBD. This model uses ethanol to remove the protective mucous and 2,4,6-trinitrobenzenesulfonic acid (TNBS) to induce a chronic colitis in rats. In a related model, 2,4,6-dinitrobenzenesulfonic acid (DNBS) is used to produce a chronic inflammation and ulceration in the colon similar to the TNBS model. Both of these models have been used to measure inflammatory mediators in chronic colitis.

Figure 1:
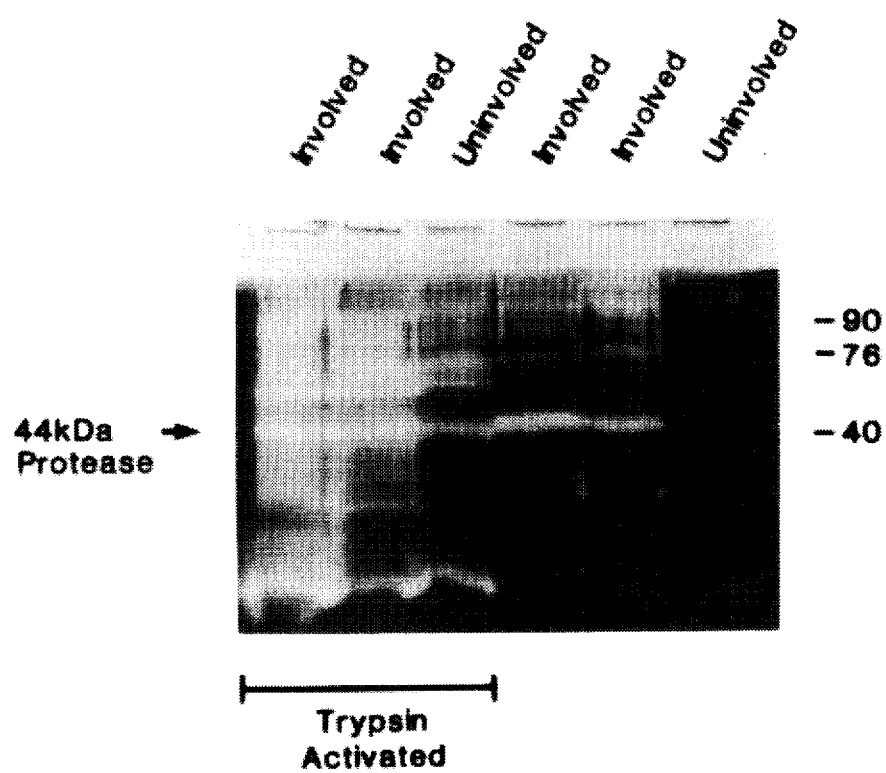
FIG. 1 shows an analysis of human biopsy samples for protease activity. Human colonic mucosal biopsy samples of uninvolved (i.e., normal appearing) and involved regions of colonic epithelium were obtained from patients with ulcerative colitis. The samples were homogenized and analyzed for protease activity on gelatin zymograms. Fifty µg of protein was loaded into each lane of the gel. Samples were untreated or activated with trypsin prior to being run on the zymogram. Involved: tissue biopsy from involved region of the colon. Uninvolved: material obtained from normal appearing colonic epithelium. The 44 kDa protease is not present in the unactivated sample obtained from normal appearing regions of the colon. However, this protease is present (without trypsin activation) in the involved regions of the colon in UC patients. Numbers on right of FIG. 1 refer to molecular weight in kDa. The arrow on left of FIG. 1 designates the position of 44 kDa protease activity.

Human biopsy samples of normal and involved regions of colonic epithelium were obtained from patients with ulcerative colitis. The samples were homogenized and analyzed for protease activity on gelatin zymograms. Fifty micrograms of protein were loaded into each lane of the gel. Samples were untreated or activated with trypsin prior to being run on the zymogram. Tissue biopsy from involved region of the colon was obtained using a brushing procedure. Material was obtained from normal, uninvolved colonic epithelium in the same manner. As shown in FIG. 1, there is an absence of the 44 kDa protease in the unactivated sample obtained from the normal colonic epithelium. Similar results were obtained with other colonic biopsy samples.

BBI and DFP are both highly effective at inhibiting the activity of proteases present in UC lesions and result in the elimination of almost all protease activity present in the sample. See FIG. 2. When the results were analyzed by scanning densitometry, the column representing the UC lesion with no protease inhibitor activity has 7.7 times more activity than the BBI column; 1.6 times more activity than the EDTA column and 10.1 times more activity than the DFP column. Pepstatin (an inhibitor of aspartic proteases) and NEM (an inhibitor of thiol proteases)'have little effect on protease activity in the UC lesions.

Figure 3:
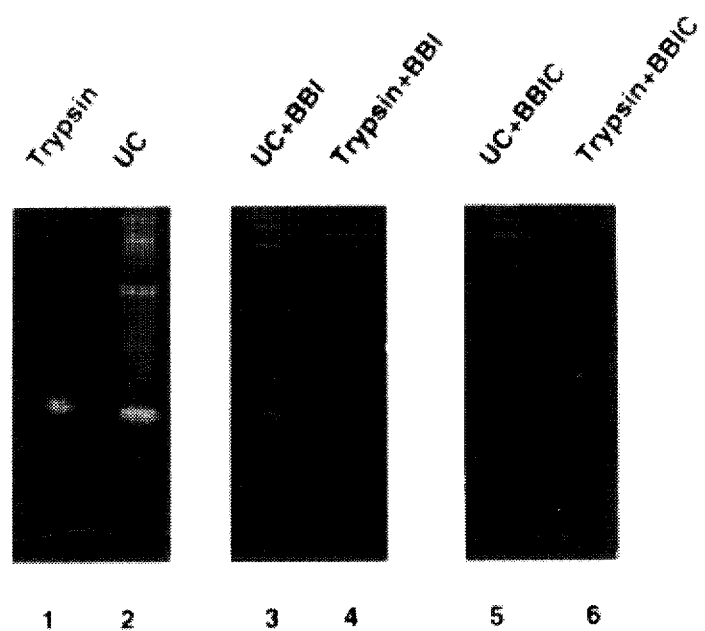
FIG. 3 shows the effects of treatments with two different BBI products (BBI and BBIC) on UC lesions from rat colon. BBI or BBIC (at 10 µg/ml) was added to some of the biopsy sample homogenates and protease activity was analyzed on gelatin zymograms. The same rat colon sample from a 14 day DNBS/ethanol treated rat was used for the protease/zymogram analyses. The gel was run at 200 V for 40 minutes and was then cut into pieces. Each gel/column was treated as follows: 1) Control-contained 5 ng trypsin; 2) UC sample incubated in Tris at pH 8.0; 3) UC sample incubated in Tris at pH 8.0 with BBI added to achieve a final concentration of 10 µg/ml; 4) Control-contained 5 ng trypsin with BBI added to achieve a final concentration of 10 µg/ml; 5) UC sample incubated in Tris at pH 8.0 with BBIC added to achieve a final concentration of 10 µg/ml; 6) Control-contained 5 ng trypsin with BBIC added to achieve a final concentration of 10 µg/ml.

Similar zymograms were analyzed to compare the effects of BBIC to that of BBI on proteolytic activities present in UC lesions. These results are shown in FIG. 3. It can be observed in FIG. 3 that BBIC is as effective as BBI in its inhibition of the proteolytic activity present in UC lesions.

Figure 2:
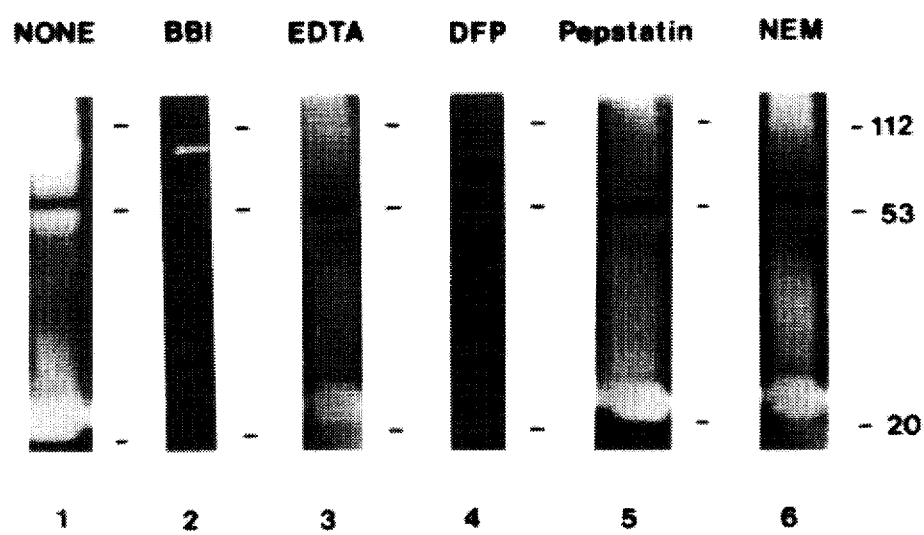
FIG. 2 shows an analysis of proteolytic activity associated with ulcerative coliris lesions in a rat model system of inflammatory bowel disease. The tissue was from a DNBS/ethanol sample at day 7. Small pieces of colon tissue were removed, weighed and placed in a 2 ml microfuge tube with 400 µl of cold phosphate buffered saline (PBS). The tissue was ground for 10 seconds (on ice) in a tissue homogenizer and PBS was then added to achieve a final concentration of 50 mg tissue per ml of PBS. The sample was then sonicated for 10 seconds on ice. The homogenized tissue was centrifuged at 14,0000× g for 5 minutes at 5° C. The supernatant was drawn off and placed into the gel wells. The gel was run and the different columns were cut off and incubated in media containing the different specific inhibitors. The results shown in this SDSpolyacrylamide gel with gelatin indicate the effects of inhibitors for specific classes of proteases. Pepstatin (an inhibitor for aspattic proteases) and NEM (an inhibitor of thiol proteases) have little effect, while EDTA (an inhibitor of metalloproteases) does have some ability to affect the proteolytic activity in the samples. DFP (an inhibitor of serine proteases; DFP is also known as nerve gas) and BBI essentially abolish the proteolytic activities present in the UC lesions. For these studies, DFP was used at 1 mM, while BBI was used at 1.25 µM; thus, BBI is effective at a considerably lower concentration than is DFP in its inhibition of the proteolytic activity in UC lesions.

The results presented in FIGS. 2 and 3 suggest that there are several different proteolytic activities present at high levels in UC lesions which are affected by BBI and BBIC. It is believed that one of the proteases playing a role in the causation of IBD and present in the UC lesions is the 44 kDa protease and that the 44 kDa protease is one of the proteases whose activity is inhibited by BBI in the rat model of UC. That BBI is able to affect the levels of expression of other potentially important proteolytic activities has been observed in other types of experiments. The levels of these particular proteolytic activities are increased in carcinogen-treated cells in both in vivo and in vitro systems and are at elevated levels in human tissue which is at higher than normal risk of cancer development. The levels of proteolytic activities in colon mucosal biopsy samples of UC patients have been determined. As shown in FIG. 4, there are elevated levels of the marker proteolytic activities in the uninvolved, i.e., normal appearing, regions of colonic mucosa in UC patients. It is believed that treatment with a composition comprising BBI will return the elevated levels of these proteolytic activities to normal levels in the uninvolved regions of the colon of UC patients. It has been observed in colon carcinogenesis studies in animals that particular proteolytic activities are elevated in DMH-treated colon mucosa and that in DMH and BBI or BBIC treated animals, there is a reduction in levels of these proteolytic activities that parallels the BBI suppression of DMH-induced colon carcinogenesis. It is believed that treatment with a composition comprising BBI will also control levels of these proteolytic activities in the normal appearing colonic mucosa of UC patients, thus preventing the inflammatory processes leading to ulcer formation. The data shown in histogram form in FIG. 4 are shown for individual patients, i.e., those with UC or normal individuals, in the following Table 1. All colon mucosal biopsy samples for those with or without evidence of IBD were taken from normal appearing areas of the colonic mucosa.

TABLE 1

Relative Fluorescent Units (RFU)/hr/μg Protein

Normal Biopsy

| | Patient | | | | |
|---|---|---|---|---|---|
| Substrate | Norm 1 | Norm 2 | Norm 3 | Mean | St. Dev. |
| Boc-Val-Pro-Arg | 24.17 | 43.23 | 38.41 | 35.27 | 9.91 |
| Boc-Val-Leu-Lys | 3.19 | 3.83 | 8.33 | 5.12 | 2.80 |
| Glt-Gly-Arg | 2.15 | 1.41 | 2.62 | 2.06 | 0.61 |

Ulcerative Colitis Biopsy

| | Patient | | | | St. |
|---|---|---|---|---|---|---|
| Substrate | UC1 | UC2 | UC3 | UC4 | Mean | Dev. |
| Boc-Val-Pro-Arg | 72.50 | 714.00 | 47.71 | 66.26 | 225.12 | 326.09 |
| Boc-Val-Leu-Lys | 20.00 | 92.40 | 8.74 | 12.83 | 33.49 | 39.55 |
| Glt-Gly-Arg | 20.58 | 41.20 | 9.69 | 4.31 | 18.95 | 16.31 |

The levels of proteolytic activity were determined as following. Colon mucosal biopsy samples were thawed on ice and homogenized in ice-cold PBS in a sterile teflon-glass homogenizer. The level of proteolytic activity was measured by incubating aliquots of sample in 0.1M Tris (pH 7.5)-5 mM $CaC_{12}$, with each of the following synthetic substrates: Boc-Val-Pro-Arg-MCA; Boc-Val-Leu-Lys-MCA; and Glt-Gly-Arg-MCA (Peninsula Laboratories, Inc., Belmont, Calif.). These substrates were selected since it is known that the proteolytic activity cleaving these substrates is affected by BBI. After a 2 hour incubation at 37° C., the reaction was terminated by dilution with 1.8 ml distilled $H_2O$. Release of the fluorescent reporter group, amino-methyl coumarin, was determined spectrophotometrically at excitation and emission wavelengths of 380 and 460 nm, respectively. Protein content was determined in accordance with the Bradford method as described in *Anal. Biochem.* 1976, 72,248–254, using bovine serum albumin as a standard. Data were standardized on the basis of protein content and expressed as proteolytic activity/µg protein. These data are presented in FIG. 4. When subjected to a t-test, adjusted to account for unequal variances using Welch's correction, p-values obtained indicated that the levels of proteolytic activity for UC patients vs. normal controls were significantly different from each other.

Similar studies were performed to determine the levels of proteolytic activity in colon mucosal biopsy samples of control rats vs. rats exposed to the chemical carcinogen, DMH, with and without BBI treatment. In these studies, animals were untreated or treated twice weekly for three weeks with DMH. The DMH dose administered (total dose, 80 mg/kg) has been shown previously to give rise to colon cancer in animals. One group of treated animals was also exposed to 0.1% dietary BBIC during and after the DMH injection period. Animals were killed one month after the last DMH injection was given. Colon biopsy samples were obtained and proteolytic activity levels were determined as described for the human mucosal biopsy samples. Data from these studies are shown in the following Table 2.

TABLE 2

| | Protease Activity/µg protein | |
|---|---|---|
| RFU/hr/Ag protein | Mean | Standard Deviation |
| CONTROL: 1 ANIMAL, 3 SAMPLES | | |
| Boc-Val-Pro-Arg-MCA | 15.97 | 0.12 |
| Boc-Val-Leu-Lys-MCA | 3.07 | 0.04 |
| Glt-Gly-Arg-MCA | 1.21 | 0.04 |
| DMH: 1 ANIMAL, 3 SAMPLES | | |
| Boc-Val-Pro-Arg-MCA | 43.43 | 0.67 |
| Boc-Val-Leu-Lys-MCA | 10.15 | 0.16 |
| Glt-Gly-Arg-MCA | 6.15 | 0.04 |
| DMH + BBI: 1 ANIMAL, 3 SAMPLES | | |
| Boc-Val-Pro-Arg-MCA | 22.22 | 0.03 |
| Boc-Val-Leu-Lys-MCA | 1.96 | 0.03 |
| Glt-Gly-Arg-MCA | 0.81 | 0.00 |

These data are also shown in FIG. 5. These results indicate a highly significant elevation in the levels of proteolytic activity one month after DMH treatment alone, while the levels of proteolytic activity are approximately normal in DMH-exposed animals treated with BBIC. Results of these studies show that at a dose of DMH known to be carcinogenic, animals have significantly elevated levels of proteolytic activity one month after the last dose of DMH was administered. Under conditions in which DMH treatment causes colon cancer in the animals, 0.1% dietary BBIC leads to a highly significant reduction in the number of animals with colon cancer and/or the number of tumors per animal. These data show that, under conditions in which dietary BBIC reduces the number of animals with colon cancer, it also decreases protease levels in the DMH-treated animals. BBIC treatment is capable of significantly reducing the DMH-elevated protease levels approximately to those observed in untreated control animals. The results of these experiments show that protease levels in the DMH+BBIC treatment group are significantly reduced when compared to the levels observed in the DMH treatment group. It is believed that the doses utilized for anti-carcinogenic activity of BBI and BBIC will also be useful for decreasing and inhibiting inflammation, with this anti-inflammatory activity being correlated with decreases in the levels of proteolytic activities.

In human trials to determine the efficacy of a composition comprising BBI in alleviating the symptoms of IBD and macroscopic inflammation as observed endoscopically in patients with UC, four different daily doses of BBIC, i.e., 100, 200, 400 and 800 Chymotrypsin Inhibitor (C.I.) units will be studied. A 200 C.I. unit dose approximates the dose of soybean protease inhibitor activity in the traditional Japanese diet. Eight patients per dose group will be studied. Patients will take BBIC in the form of pills for 3 months. They will be seen a total of 3 times during the BBIC treatment period (at the beginning of the study, at 1.5 months into the study, and at 3 months after the BBIC treatment has begun) and at 1 month after the end of the BBIC trial period. Flexible sigmoidoscopy and biopsy procedures will be performed before BBIC therapy begins and at the end of the three month trial period. Three biopsy samples will be taken for analyses of: 1) proteolytic activities as determined by hydrolysis of the substrates Boc-Val-Pro-Arg, Boc-Val-Leu-Lys, and Glt-Gly-Arg; 2) specific proteolytic activity of the 44 kDa protease; and 3) levels of markers of inflammation such as cytokines IL-1β', IL-6, IL-8 and TNF-2 and lipid peroxidation. One biopsy sample taken from a normal appearing area of colonic mucosa in patients with UC will be used for substrate hydrolysis assays while the analyses for the levels of the 44 kDa protease and markers of inflammation will utilize the two biopsy samples taken from the most severely affected regions of colonic mucosa. Effects of BBIC on symptoms of IBD will be correlated with effects of these markers. The uptake of BBI metabolites into the blood and excretion into the urine will also be performed as part of the BBIC multiple dosing protocol in UC patients. All urine samples will be collected over a 24 hour period following administration of BBIC at the beginning, middle and end of the 3 month study.

Patients were administered a BBIC composition at four different doses (25, 100, 200 and 400 C.I. units) as a mouthwash which was swallowed. Blood samples were taken from the patients before treatment with BBIC and approximately 4 weeks after BBIC treatment. As part of the analysis of the blood samples, liver function analyses were performed. Concentrations of serum glutamic-oxaloacetic transaminase (SGOT) and serum glutamic-pyruvic transaminase (SGPT) above the normal range are a common sign of hepatic inflammation. In the three subjects in the study having elevated SGOT or SGPT, BBIC treatment was found to return these concentrations to normal. Normal concentrations of SGOT range from 5 to 40 U/L in these studies. Normal concentrations of SGPT range from 7–56 U/L in these studies. Data from this study are provided in Table 3.

TABLE 3

| Patient I.D. (Dose of BBIC) | Blood Sample | SGOT Assay (U/L) | SGPT Assay (U/L) |
|---|---|---|---|
| K.B. (25 C.I. units) | before BBIC administration | H44 | 49 |
| | after BBIC administration | 40 | 28 |
| P.D. (200 C.I. units) | before BBIC administration | H55 | H71 |
| | after BBIC administration | 30 | 24 |
| J.M. | before BBIC | H44 | 53 |

TABLE 3-continued

| Patient I.D. (Dose of BBIC) | Blood Sample | SGOT Assay (U/L) | SGPT Assay (U/L) |
|---|---|---|---|
| (400 C.I. units) | administration after BBIC administration | 20 | 26 |

The "H" next to the number indicates "high" in these clinical laboratory assays. The effect of BBIC treatment in returning the elevated concentrations of SGOT and SGPT to normal values is consistent with an anti-inflammatory effect of BBI compositions.

The following examples illustrate the practice of this invention and the characterization and utility of products resulting therefrom. They are provided for illustrative purposes only and are not intended to limit the invention.

EXAMPLES

Chemicals

The DNBS was purchased from ICN. Gelatin was purchased from DIFCO (Detroit, Mich.). The EDTA, ethanol, DFP (diisopropyl fluorophosphate), trypsin and pepstatin were obtained from Sigma (St. Louis, Mo.). Bowman-Birk Inhibitor Concentrate (BBIC) was obtained from Central Soya (Ft. Wayne, Ind.); and purified BBI was obtained from BBIC by DEAE ion-exchange chromatography.

Colon samples

Thirty-eight male, virus antibody free, Sprague-Dawley rats (250–300 g) were purchased from Charles River Laboratories and were housed in microisolator cages on aspen chip bedding according to standards set by the *Guide for the Care and Use of Laboratory Animals*. They were fed Laboratory Rodent Diet #5001 from Purina Mills (St. Louis, Mo.). The animals were divided into four groups: a negative or procedural control group; a positive control group given a saline enema; a vehicle control group that was given 0.25 ml of ethanol; and a DNBS/ethanol group given 30 mg of DNBS in 0.25 ml of ethanol. The compounds were given as an enema with a metal gavage needle inserted rectally until the tip was about 8 cm from the anus, which is about the location of the splenic flexure. The animals were restrained for approximately 30 seconds after installation. There were 3 animals in the procedural control group; an animal was euthanized with $CO_2$ on days 1, 3 and 7. There were 5 animals in the saline control group; 1 rat was euthanized on day 1, 2 rats on day 7, and 2 rats on day 14. There were 15 animals in each of the remaining treated groups. Five animals from each group were euthanized with $CO_2$ on day 1, day 7, and day 14, post-enema. All animals were weighed while alive on days 1, 1, 7 and 14. The proximal 8 cm of colon was removed and opened longitudinally. The feces were removed and the tissue was rinsed in saline. The gross lesions in the colons were scored on the basis of ulceration, inflammation and hemorrhage (MG). The colon was again cut lengthwise with half of the tissue being placed into formalin and the other half placed on dry ice and then frozen at −80° C. until it was assayed for protease activity.

Histopathology

The formalin fixed colon tissue was processed in a conventional fashion: paraffin embedded and stained with hematoxylin and eosin. A sample from each end of the piece of colon and 2 samples from the center of the colon were examined for each tissue and graded as follows:

0=normal

1a=focal erosion (damage limited to the surface epithelium)
1b=inflammation limited to the mucosa
2a=focal ulceration
2b=transmural inflammation
3a=focal ulceration and transmural inflammation
3b=extensive erosion and transmural inflammation
4=extensive ulceration or coagulative necrosis bordered by normal mucosa and transmural inflammation
5a=extensive ulceration and transmural inflammation involving the entire section
5b=extensive mucosal coagulative necrosis and transmural inflammation involving the entire section Definitions Erosion: part of the mucosa is missing but there is mucosa remaining overlying the muscularis mucosa Ulceration: the mucosa is missing to the level of, or deeper than the muscularis mucosa Transmural: involving the mucosa, submucosa, muscularis layers and the serosa Tissue sampling and homogenization Tissue samples taken from the middle of the piece of colon or from the center of the ulcer were designated as "C"; samples taken midway between the center and the end of the tissue were designated as "I"; and the sample from the end of the tissue sample was designated as "E". A small piece of tissue was collected from a section of colon, weighed and placed in a 2 ml microfuge tube with 400 µl of cold phosphate buffered saline (PBS). The tissue was ground for 10 seconds on ice by a Tekmar Ultra-Turrax homogenizer (Cincinnati, Ohio). Enough PBS was added to achieve a ratio of 50 mg tissue per milliliter of PBS. While still on ice, the sample was sonicated by a Fisher Sonic Dismembranator (Farmingdale, N.Y.) for 10 seconds. The homogenated tissue was centrifuged at 14,000× g for 5 minutes at 5° C. The supernatant was kept on ice until it was needed.

Zymogen protease assays

Twelve percent sodium diodecyl sulfate (SDS) polyacrylamide gels of 0.75 mm thickness were prepared containing 0.1% gelatin. A 2% gelatin stock was prepared in advance by dissolving gelatin in warm distilled water. Samples were placed in the gel wells in standard SDS-gel-loading buffer that contained 0.1% SDS but lacked beta-mercaptoethanol. They were not boiled prior to loading. The gels were run at 200 V for 40 minutes in a Bio-Rad Mini Protean II apparatus and then soaked in distilled water containing 2% Triton X-100 on a gyrorotary shaker for 15 minutes at 20° C. Gels that were to be placed into a buffer containing EDTA were soaked in 2% Triton X-100 with 10 mM EDTA in distilled water. The gels were transferred to incubation buffers and incubated for 16 hours at 38.5° C., stained in amido black, followed by desraining in water-methanol-acetic acid (7% methanol and 5% acetic acid per liter).

Incubation buffers

Determination of pH optima was done by preparing incubation buffers at pH of 5.2, 8, 9 and 10.2. A 50 mM acetate buffer, pH 5.2 and a 50 mM Glycine-NaOH, pH 10.2 were prepared in advance. Buffers of pH 8 and pH 9 were also prepared by using 50 mM Tris-HCL.

Protease specific inhibitors were prepared. Ten µof pure stock Diisopropyl fluorophosphate (DFP) was put into 50 ml of 50 mM Tris as an inhibitor for serine proteases. A 100 mM stock solution of N-ethylmaleimide (NEM) in ethanol was prepared in advance and was added to 50 mM Tris, pH 8.0, for a concentration of 1 mM as an inhibitor for thiol proteases. A 100 mM stock of pepstatin in methanol was prepared in advance and was added to 50 mM Tris, pH 8.0, for a concentration of 1 mM as an inhibitor for acid proteases. A 200 mM stock of EDTA in distilled water was prepared in advance and was added to 50 mM Tris, pH 8.0, for a concentration of 10 mM as an inhibitor for metalloproteases. Aliquots of BBI containing 500 mg per ml of water were prepared in advance and frozen at −20° C. until needed. The aliquot of 500 mg of BBI was then added to 49 ml of Tris, pH 8.0, as an inhibitor for proteases inhibited by BBI.

Analysis of tissues

Tissue from each test group is analyzed as follows:

| Day | Negative Control | Saline Control | Ethanol Control | DNBS/ Ethanol |
|---|---|---|---|---|
| 1. | histopath pH optima inhibitors | histopath pH optima inhibitors C, I, E, neg | histopath pH optima inhibitors C, I, E, neg | histopath pH optima inhibitors C, I, E, neg |
| 7. | histopath pH 8 | histopath pH optima inhibitors C, I, E, neg | histopath pH optima inhibitors C, I, E, neg | histopath pH optima inhibitors C, I, E, neg |
| 14. | histopath | histopath pH optima inhibitors C, I, E, neg | histopath pH optima inhibitors C, I, E, neg | pH optima inhibitors C, I, E, neg |

Tissue sections
C: center of lesion or center of colon section
I: intermediate piece between center and end section
E: end piece of colon tissue
neg: sample from negative control Administration of BBIC mouthwash to inhibit hepatic inflammation BBI Concentrate (BBIC) from soybeans was supplied from Central Soya as a fine powder, C.I. activity=100 mg/g. The BBIC is administered as a mouthwash. This product is designed to be a stable mouthwash solution that provides extended mucosal contact time, is palatable, easy to administer and suitable for low cost mass production. A saliva substitute provides the solution with the necessary viscosity to increase mucosal contact time and bioavailability, and has been shown to provide sustained release of many compounds. In the formulation prepared for these experiments, BBI Concentrate (BBIC), the "saliva substitute" (Roxane Laboratories, Inc. Columbus, Ohio) and water are included.

Each 20 milliliter dose was supplied to the research subjects in two separate containers. Each 2 ounce bottle contained 14 milliliters of Saliva Substitute and 6 milliliters of water. BBIC (25 and 100 C.I.) was provided in a separate container, for admixture prior to administration. The 200 and 400 unit doses were administered in 40 ml and 80 ml mouthwash volumes.

Immediately after mixing the components and shaking the suspension for 30 seconds, each subject self-administered the full 20 milliliters (or 40 or 80 ml) of mouthwash, swished for 1 minute and then swallowed. Each subject was required to drink 6 oz. of water after administration of BBIC to aid with gastrointestinal absorption.

Prior to administration of BBIC, a base-line (zero time) blood sample was withdrawn through an intravenous line. Approximately 4 weeks after the administration of the BBIC another blood sample was taken. SGOT and SGPT levels were measured in each blood sample in accordance with well known procedures.

What is claimed is:

1. A method for treating inflammatory bowel disease in an animal comprising administering an effective amount of BBI to an animal having an inflammatory bowel disease.

2. The method of claim 1 wherein BBI is administered in combination with a pharmaceutically acceptable carrier.

3. A method of treating hepatic inflammation in an animal comprising administering an effective amount of BBI to an animal having hepatic inflammation.

4. The method of claim 3 wherein BBI is administered in combination with a pharmaceutically acceptable carrier.

* * * * *

UNITED STATES PATENT AND TRADEMARK OFFICE
CERTIFICATE OF CORRECTION

PATENT NO. : 5,614,198

DATED : Mar 25, 1997

INVENTOR(S) : Kennedy et al.

It is certified that error appears in the above-indentified patent and that said Letters Patent is hereby corrected as shown below:

At col 2, line 53, after "PtI-1", please delete "$\geqq$" and insert therefor --$\geq$--.

At col 2, line 53, after "BBI", please delete ">" and insert therefor --$\geq$--.

At col 4, line 5, please delete "aspattic" and insert therefor --aspartic--.

At col 7, line 56, after "proteases)", please delete the apostrophe.

At col 8, line 60, please delete "$CaC_{12}$" and insert therefor --$CaCl_2$--.

In Table 2, at col 9, line 31, after "RFU/HR/", please delete "Ag" and insert therefor --$\mu$g--.

At col 12, line 61, after "Ten", please delete "$\mu$of" and insert therefor --$\mu$l of--.

In the Table at col 13, line 23, after "14.", please delete "histopath" from column 1.

UNITED STATES PATENT AND TRADEMARK OFFICE
CERTIFICATE OF CORRECTION

PATENT NO. : 5,614,198
DATED : March 25, 1997
INVENTOR(S) : Kennedy, et. al.

It is certified that error appears in the above-indentified patent and that said Letters Patent is hereby corrected as shown below:

In the Table at col13, line 23, after the second occurrence of "histopath", please insert "histopath" in the last column.

Signed and Sealed this

Twenty-third Day of September, 1997

*Attest:*

*Attesting Officer*

BRUCE LEHMAN

*Commissioner of Patents and Trademarks*